US00PP12400P2

(12) United States Plant Patent
Pinney, Jr.

(10) Patent No.: US PP12,400 P2
(45) **Date of Patent: *Feb. 12, 2002**

(54) BIRCH TREE NAMED 'CENCI'

(75) Inventor: Thomas S. Pinney, Jr., Sturgeon Bay, WI (US)

(73) Assignee: Evergreen Nursery Company, Inc., Sturgeon Bay, WI (US)

( * ) Notice: Subject to any disclaimer, the term of this patent is extended or adjusted under 35 U.S.C. 154(b) by 0 days.

(21) Appl. No.: 09/395,054

(22) Filed: Sep. 13, 1999

(51) Int. Cl.[7] ..... A01H 5/00

(52) U.S. Cl. ..... Plt./216
(58) Field of Search ..... Plt./216

*Primary Examiner*—Bruce R. Campell
*Assistant Examiner*—Susan B. McCormick
(74) *Attorney, Agent, or Firm*—W. Dennis Drehkoff; Ladas & Parry

(57) ABSTRACT

A new and distinct cultivar of *Betula papyrifera* named 'Cenci' characterized by its tight, oval, compact growth habit, slow to moderate growth rate, white, large, shaggy, persisting exfoliating bark when mature and high resistance to the Bronze Birch Borer.

4 Drawing Sheets

The present invention comprises a new and distinct cultivar of a birch tree, botanically known as *Betula papyrifera*, and is hereto referred to by the cultivar name 'Cenci'.

BACKGROUND OF THE INVENTION

'Cenci' was discovered by the inventor in a group *Betula papyrifera* in a provenance test plot planted in Wooster, Ohio in 1986. 'Cenci' was originated from the open pollinated cross in a birch selection/breeding program on Evergreen Nursery Company property. The female parent was *Betula papyrifera*. The male parent is unknown. 'Cenci' was first noticed with a tight, oval, compact growth habit, white large, shaggy, persisting exfoliating bar and a high resistance to the Bronze Birch Borer. The cultivar has been asexually reproduced in Sturgeon Bay, Wis. and Wooster, Ohio. Presently, reproduction is accomplished by micropropagation or tissue culture propagation by the inventor from the initial selection in Sturgeon Bay, Wis. Horticultural examination of selected units has demonstrated that the combination of characteristics has herein disclosed for 'Cenci' are firmly fixed and retained through its successive generations of asexual reproduction. 'Cenci' has been observed in Sturgeon Bay, Wis., and Wooster, Ohio, since 1986 and characteristics have been stably maintained. The cultivar reproduced true to type. The new cultivar has not been observed under all possible environmental conditions. The phenotype may vary somewhat with variations in environment such as temperature, day length and light intensity, without a change in the genotype of the new cultivar. The following observations, measurements and comparisons describe the plants grown in Sturgeon Bay, Wis. under natural field conditions which approximate those generally used in commercial growing operations.

SUMMARY OF THE INVENTION

The following traits have been repeatedly observed and are determined to be basic characteristics of 'Cenci' which in combination distinguish this birch tree as a new and distinct cultivar:

1. Distinctive tight, oval, compact growth habit with a good central leader and branching angles about 35–40°.

2. Bark color changes as the tree matures; from brown turning to white.
3. White, large, shaggy, persisting exfoliating bark when mature.
4. High resistance to the Bronze Birch Borer.
5. Slow to moderate growth rate.

The new cultivar can be compared to the non patented *Betula papyrifera* for the foregoing characteristics differ from the nonpatented variety in that the nonparented variety has variable resistance to the Bronze Birch Borer, has a loose oval growth habit and the bark exfoliates in smaller pieces.

BRIEF DESCRIPTION OF THE DRAWINGS

The accompanying color photographs show typical characteristics of 'Cenci', with colors being as true as possible with illustration of this type.

DETAILED BOTANICAL DESCRIPTION

Figure 1:
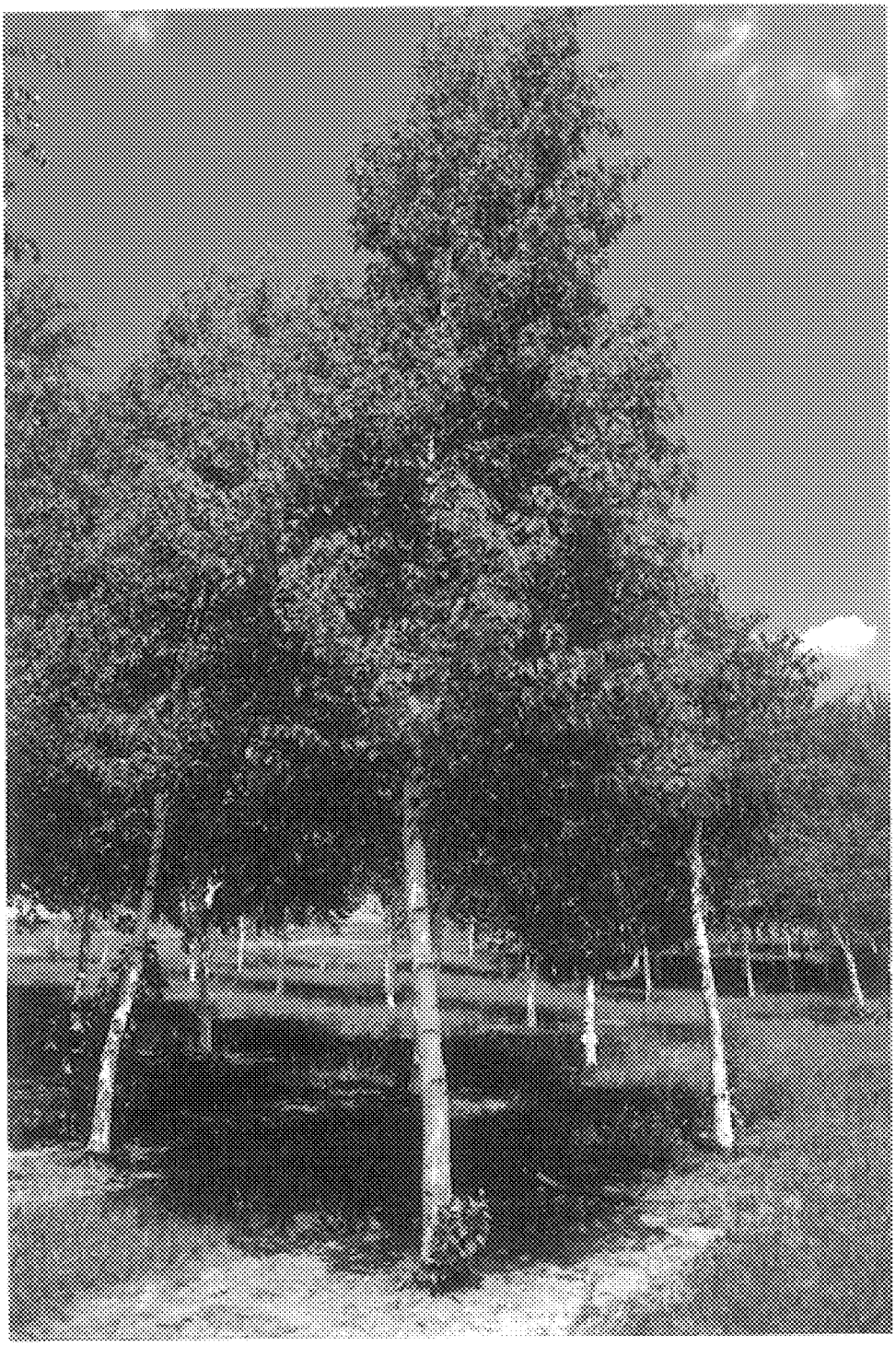
FIG. 1 is the side view a specimen of 'Cenci' showing the tight, oval, compact growth habit.
Figure 2:
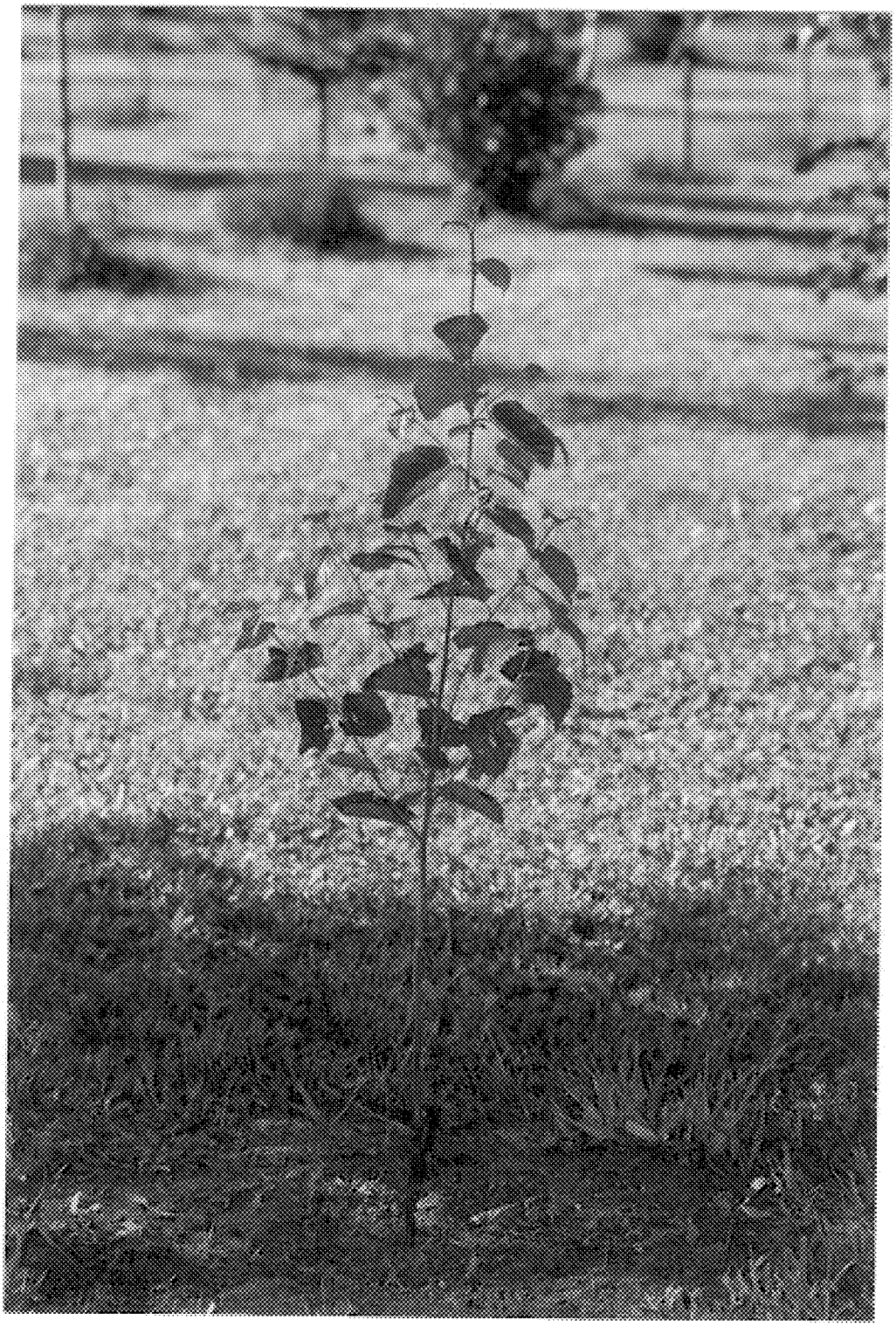
FIG. 2 is a side view of an immature tree of my new variety showing the typical tight, oval, compact growth habit.
Figure 3:
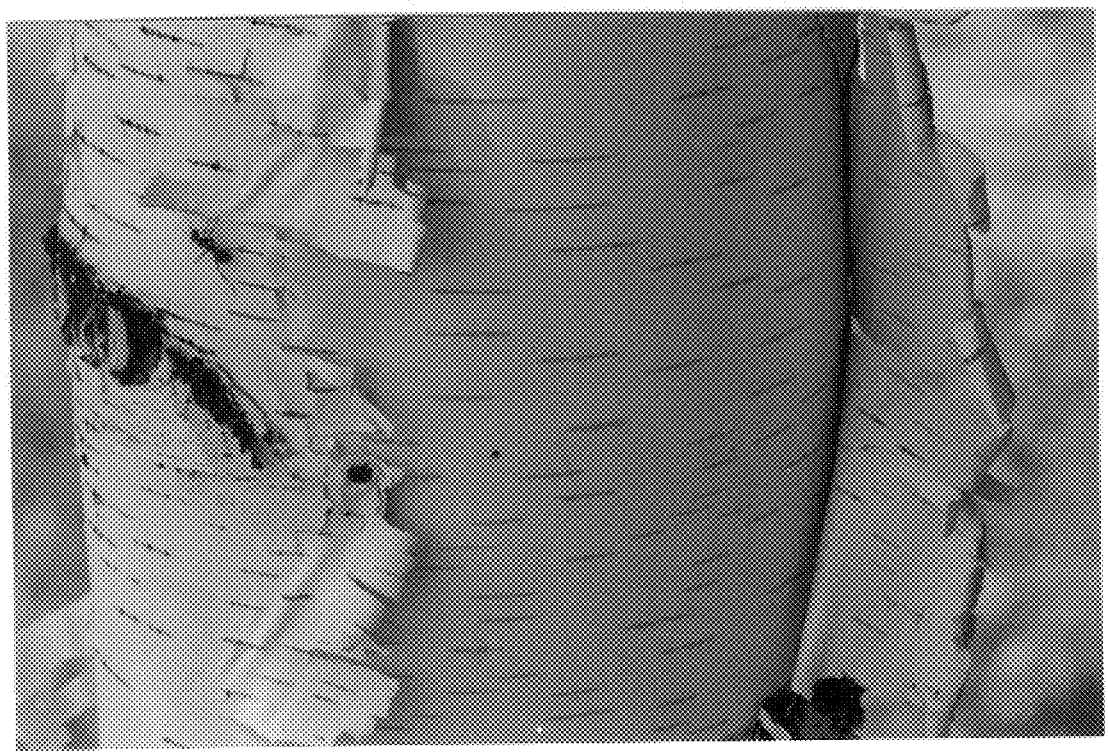
FIG. 3 shows the white, large, shaggy, persistently exfoliating bark.
Figure 4:
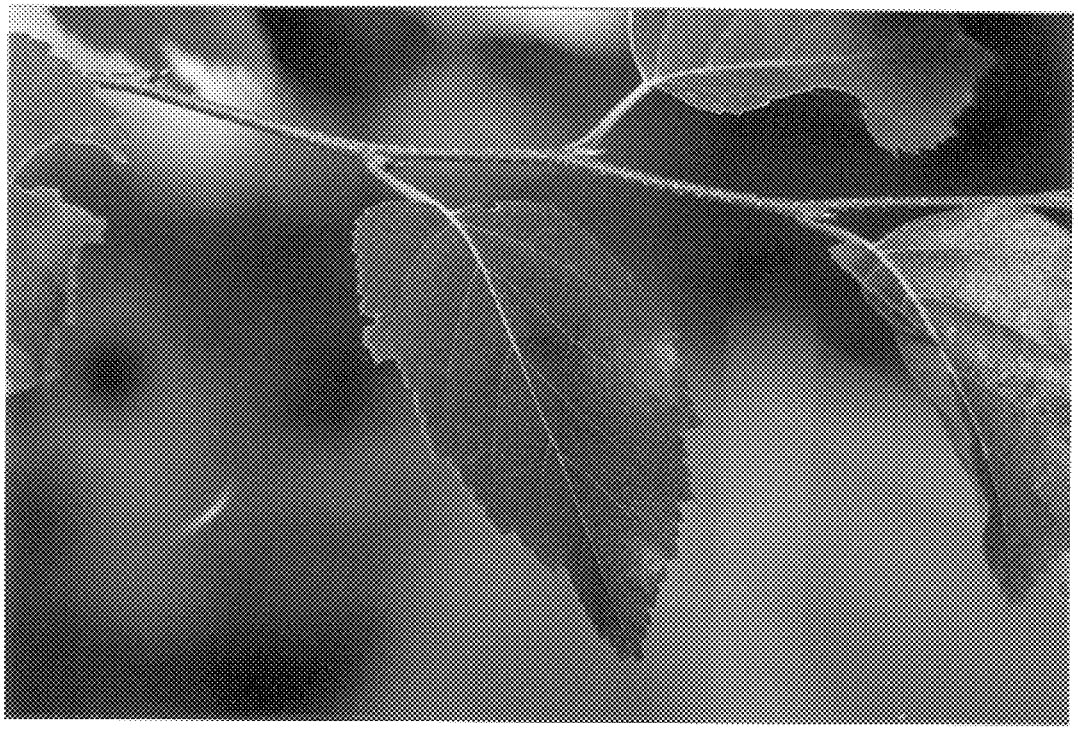
FIG. 4 shows a close-up of the upperside of a leaf.
Figure 5:
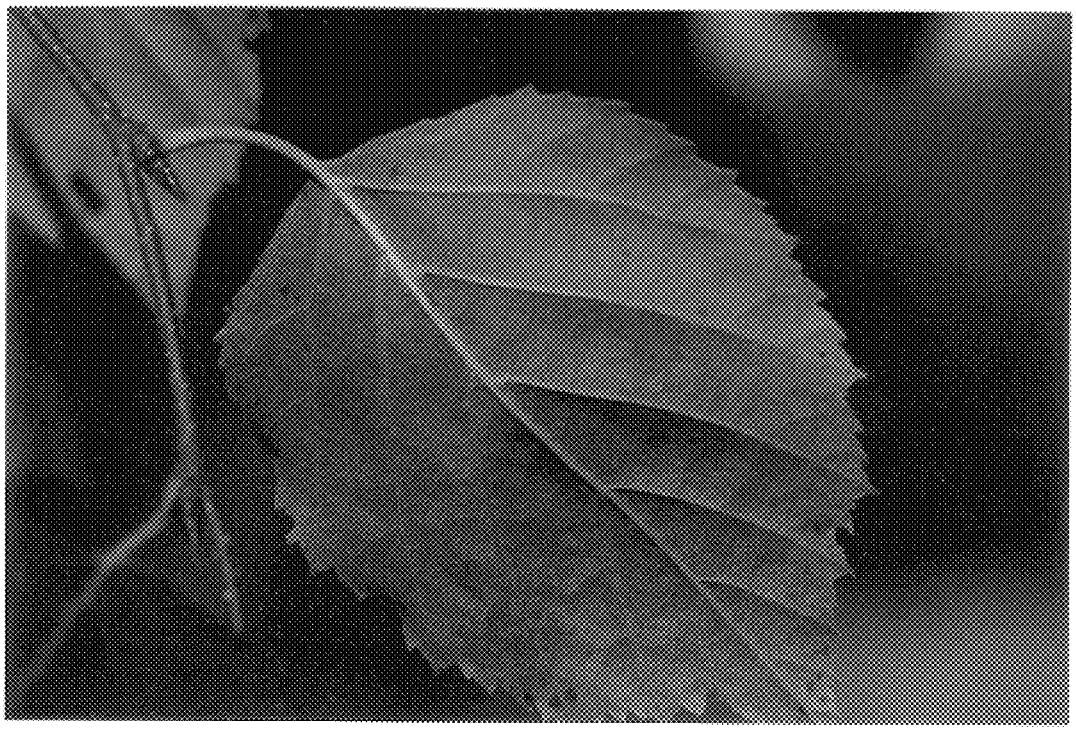
FIG. 5 shows a close-up of the underside of a leaf.

In the following description, color references are made to The Royal Horticultural Society (R.H.S.) Color Chart. The color values were determined in natural light in August 1999 in Sturgeon Bay, Wis.

Classification:

*Botanical.*—*Betula papyrifera* 'Cenci'.

Parentage:

*Origin.*—Found as a seedling in a group of *Betula papyrifera* in a provenance test plot in Wooster, Ohio in 1994.

*Parentage.*—Seed parent: *Betula papyrifera*. Pollen parent: Unknown.

Tree:

*Trunk.*—Single-trunked tree. Size: Diameter at age 10 is approximately 11.1 cm. at 1.2 m above the ground. The height is 6.6 m.

Bark at maturity: White, fine textured close to (R.H.S 155-C) semi-exfoliating to greyed-orange bark (R.H.S. 165-C).

*Branches.*—Angle of attachment: 35–40°. Spacing: Between whorls 10–15 cm. Size: at a tree size of 2.4 m, 3–4 cm. Bark: Color changes age: at $4^{th}$ year, from brown (R.H.S.-[175-A] (200D) turning to white close to (R.H.S. 155-D) with large, shaggy, persisting exfoliation, fine texture. Lenticels: Small but numerous, size 1–2 mm×1 mm. Color: (R.H.S. 177-B).

*Height.*—6.6 m at about 10 years of age.

*Growth habit or Form.*—Tight, oval compact; when tree is 6.6 m high, it is about 3.6 m wide. Growth rate: slow to moderate, about 0.5–1.0 meters per year, depending on summer temperature, fertility and water availability.

Foliage: Size of leaf: Length: with petiole 8–12 cm, without petiole 7–10 cm; Width: 5–7 cm; Arrangement: Alternate; Shape of leaf: Margin: serrate, rounded base, ovate with an acute apex and double serrate margins; Texture: Smooth, Ribs and veins: mid rib with 12–14 veins sub opposite (RHS 145B). Pubescence distribution: on underside of mid rib and in axils of veins; Quantity: Singles and some spurs with 2 leaves, approximately 25–30 leaves/50 cm of stem. Color: upperside, dark green (R.H.S. 137A), underside, dark green (R.H.S. 147B). Petiole: Length: 1–2 cm., Diameter: 1.5–2. mm; Color: (RHS 178-D). No stipules.

Disease and pest resistance: High resistance to Bronze Birch Borer as compared with other trees in an area of heavy Birch Bar Borer infestation in Wooster, Ohio and Sturgeon Bay, Wis. Highly resistant to Leafhoppers.

Disease & pest susceptibility: Moderately susceptible to leafminor

Winter hardness/drought/heat resistance: Winter hardiness in Zone 3 and good drought/heat resistance in Zone 7.

Flowers: No

Reproductive organs: Male catkins borne at end of branches, female catkins are borne upright and several nodes behind male catkins.

What is claimed is:

1. A new and distinct cultivar of birch tree named 'Cenci' as illustrated and described.

* * * * *